US011335460B2

(12) United States Patent
Guo et al.

(10) Patent No.: US 11,335,460 B2
(45) Date of Patent: May 17, 2022

(54) NEURAL NETWORK BASED SELECTION OF REPRESENTATIVE PATIENTS

(71) Applicant: International Business Machines Corporation, Armonk, NY (US)

(72) Inventors: Shi Jing Guo, Beijing (CN); Xiang Li, Beijing (CN); Hai Feng Liu, Beijing (CN); Zhi Qiao, Beijing (CN); Guo Tong Xie, Beijing (CN); Shi Wan Zhao, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 228 days.

(21) Appl. No.: 15/807,931

(22) Filed: Nov. 9, 2017

(65) Prior Publication Data
US 2019/0138692 A1 May 9, 2019

(51) Int. Cl.
*G16H 50/20* (2018.01)
*G16B 20/00* (2019.01)
*G16H 50/70* (2018.01)
*G06N 7/00* (2006.01)

(52) U.S. Cl.
CPC ............ *G16H 50/20* (2018.01); *G16B 20/00* (2019.02); *G16H 50/70* (2018.01); *G06N 7/005* (2013.01)

(58) Field of Classification Search
CPC ......... G16H 50/20; G16B 20/00; G06N 7/005
USPC .......................................................... 705/2
See application file for complete search history.

(56) References Cited

U.S. PATENT DOCUMENTS

| 7,809,660 B2* | 10/2010 | Friedlander ............ G16H 10/60 706/45 |
| 2010/0016743 A1 | 1/2010 | Syed et al. |
| 2011/0224565 A1* | 9/2011 | Ong ........................ A61B 5/361 600/509 |
| 2016/0247061 A1* | 8/2016 | Trask ........................ G06N 3/04 |
| 2016/0300026 A1 | 10/2016 | Bogoni et al. |
| 2016/0321427 A1 | 11/2016 | Bogoni et al. |
| 2018/0144465 A1* | 5/2018 | Hsieh ........................ G06N 3/08 |

FOREIGN PATENT DOCUMENTS

| CN | 101911078 B | 1/2016 | |
| EP | 1894131 B1 * | 1/2013 | ............ G16B 25/00 |
| WO | 2016022438 A1 | 2/2016 | |

OTHER PUBLICATIONS

Zhao, J., & Henriksson, A. (Jul. 21, 2016). Learning temporal weights of clinical events using variable importance. BMC Medical Informatics and Decision Making, 16(S2). doi: 10.1186/S12911-016-0311-6 (Year: 2016).*

(Continued)

*Primary Examiner* — Joshua B Blanchette
*Assistant Examiner* — Winston Furtado
(74) *Attorney, Agent, or Firm* — Amin, Turocy & Watson, LLP

(57) ABSTRACT

Techniques for identifying representative patients from a patient group are provided. Based on an outcome of interest, one or more patients can be grouped according to phenotyping features associated with the outcome of interest. Additionally, in response to grouping the one or more patients, a representative patient of the one or more patients can be determined based on values associated with the phenotyping features.

18 Claims, 10 Drawing Sheets

(56) References Cited

OTHER PUBLICATIONS

Zhao, J., & Henriksson, A. (2016). Learning temporal weights of clinical events using variable importance. BMC medical informatics and decision making, 16(2), 71. (Year: 2016).*

Exponential smoothing. (Apr. 14, 2016). Retrieved from https://en.wikipedia.org/wiki/Exponential_smoothing (Year: 2016).*

Widdows, D., & Cohen, T. (Oct. 23, 2015). Reasoning with vectors: A continuous model for fast robust inference. Logic Journal of IGPL, 23(2), 141-173. doi: 10.1093/jigpal/jzu028 (Year: 2015).*

Widdows,D.,&Cohen,T. (Oct. 23, 2015).Reasoningwithvectors:Acontinuousmodelforfastrobustinference.LogicJournalofIGPL,23(2),141-173.doi:10.1093/igpaljzu028. (Year: 205).*

Kartoun, "A Methodology to Generate Virtual Patient Repositories," 10 pages. Retrieved on Oct. 5, 2017. https://arxiv.org/ftp/arxiv/papers/1608/1608.00570.pdf.

Miotto et al., "Deep Patient: An Unsupervised Representation to Predict the Future of Patients from the Electronic Health Records," May 2016, Macmillan Publishers Limited, 13 pages. https://www.ncbi.nlm.nih.gov/pmc/articles/PMC4869115/.

"Sampling (statistics)," Wikipedia, 19 pages. Retrieved on Oct. 26, 2017. https://en.wikipedia.org/wiki/Sampling_(statistics).

Britz, "Recurrent Neural Networks Tutorial, Part 1—Introduction to RNNs," Sep. 17, 2015, 10 pages. http://www.wildml.com/2015/09/recurrent-neural-networks-tutorial-part-1-introduction-to-rnns/.

Bahdanau et al., "Neural Machine Translation by Jointly Learning to Align and Translate," 3 pages. Retrieved on Oct. 26, 2017. https://arxiv.org/abs/1409.0473.

* cited by examiner

NEURAL NETWORK BASED SELECTION OF REPRESENTATIVE PATIENTS

BACKGROUND

The subject disclosure relates to neural networks, and more specifically, to neural network selection of representative patients based on contextual data.

SUMMARY

The following presents a summary to provide a basic understanding of one or more embodiments of the disclosure. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate neural network selection of representative patients based on contextual data are described.

According to an embodiment, a system can comprise a memory that stores computer executable components, and a processor that executes the computer executable components stored in the memory. The computer executable components of the system can comprise a grouping component that, based on an outcome of interest, groups one or more patients according to phenotyping features associated with the outcome of interest. The computer executable components of the system can also comprise a neural network component that, in response to grouping the one or more patients, determines a representative patient of the one or more patients based on values associated with the phenotyping features.

According to another embodiment, a computer program product for employing neural networks to discover representative patients can comprise a computer readable storage medium having program instructions embodied therewith. The program instructions can be executable by a processor and the processor can group one or more patients according to phenotyping features associated with an outcome of interest based on the outcome of interest. The program instructions can also be executable to determine, by the processor, a representative patient of the one or more patients based on values associated with the phenotyping features in response to grouping the one or more patients.

According to yet another embodiment, a computer-implemented method is provided. The computer-implemented method can comprise grouping, by a device operatively coupled to a processor, one or more patients according to phenotyping features associated with an outcome of interest based on the outcome of interest. The computer-implemented method can also comprise, determining, by the device, a representative patient of the one or more patients based on values associated with the phenotyping features in response to grouping the one or more patients.

In some embodiments, one or more of the above elements described in connection with the systems, computer-implemented methods and/or computer program programs can be embodied in different forms such as a computer-implemented method, a computer program product, or a system.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Electronic health records (EHR) are increasingly being used for clinical analysis and research. However, EHRs can contain inaccurate data, which can lend to incorrect analysis. For a clinical analysis, the data can be described in reference to context. The context can comprise subject patients, clinical outcomes of interest, risk factors, and/or health indicators. Therefore, individual representative patients can be determined from aggregated data (e.g., patient count, feature distribution, etc.). Thus, the aggregated data can be utilized to determine a subset of representative patients based on relevant data in regards to a specific clinical context.

One or more embodiments described herein can facilitate neural network based selection of representative patients based on contextual data. One or more embodiments described herein can also include systems, computer-implemented methods, apparatus, and computer program products that facilitate neural network selection of representative patients based on contextual data.

Figure 1:
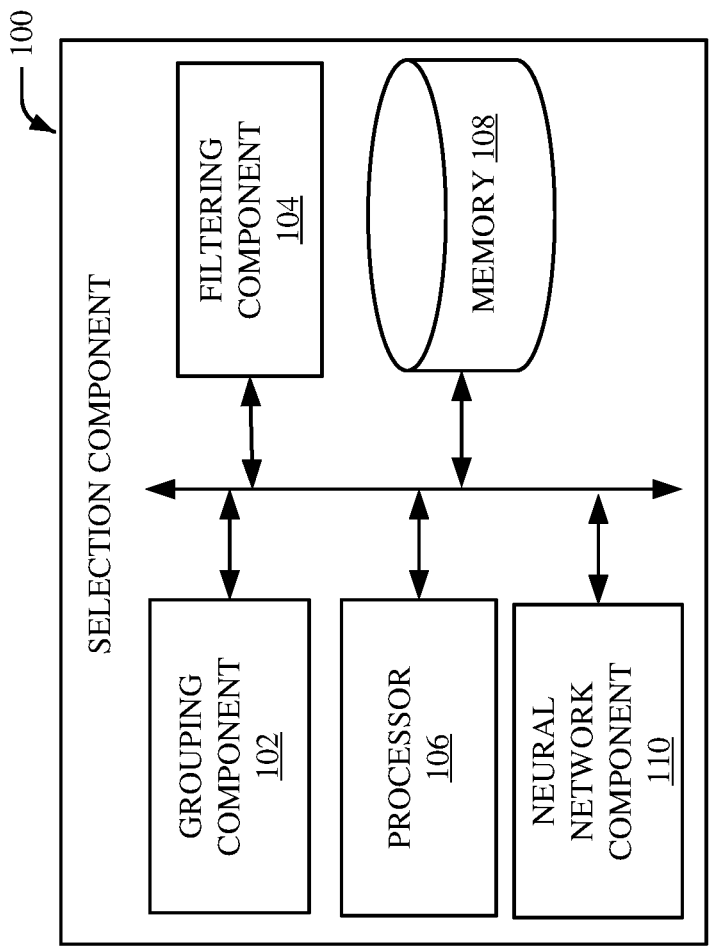
FIG. 1 illustrates a block diagram of an example, non-limiting system that facilitates neural network based selection of representative patients in accordance with one or more embodiments described herein.

FIG. 1 illustrates a block diagram of an example, non-limiting system that facilitates neural network based selection of representative patients in accordance with one or more embodiments described herein. In various embodiments, the selection component 100 can be associated with or included in a data analytics system, a data processing system, a medical system, a health monitoring system, a network system, a computer network system, or the like.

In one embodiment, the selection component 100 can select representative patients based on contextual data. For example, the selection component 100 can comprise several sub-components (e.g., a grouping component 102, a filtering component 104, a neural network component 110, etc.), which can be electrically and/or communicatively coupled to one another in various embodiments. It should also be noted that in alternative embodiments that other components including, but not limited to the sub-components, processor 106, and/or memory 108, can be external to the selection component 100.

Aspects of the processor 106 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described by the selection component 100. In an aspect, the selection component 100 can also include memory 108 that stores computer executable components and instructions.

The selection component 100 can be employed to use hardware and/or software to solve problems that are highly technical in nature (e.g., neural network analysis, time-decay weighting, data filtering, comparing of phenotyping features within corpora composed of millions of phenotyping features, etc.), that are not abstract and that cannot be performed as a set of mental acts by a human due to the processing capabilities needed to facilitate neural network selection of representative patients, for example. Further, some of the processes performed may be performed by a specialized computer for carrying out defined tasks related to memory operations. For example, a specialized computer can be employed to carry out tasks related to time-decay analysis for weighting phenotype features or the like.

Several phenotyping features can be relevant to determining a clinical outcome of interest. For example, given an atrial fibrillation (AF) patient with years of records, it can be difficult to identify the phenotyping features associated with the patients AF. However, such phenotyping features can comprise: last systolic blood pressure (SBP), minimum SBP, maximum SBP, average SBP, medication used, unknowns, etc. However, phenotyping features can be shared across a set of related outcomes for patients with the same or similar diseases. For instance, phenotypes such as age, weight, SBP, history of diabetes, hypertension, etc., can all be associated with related outcomes such as: strokes, myocardial infarctions, heart failure, atrial fibrillation, etc. Thus, to track a phenotype of a specific patient, the types of phenotyping features which are relevant or irrelevant to a specific outcome can be utilized. Different phenotyping features can be assessed against the outcome via the following process: 1) prepare patient data as an event sequence, 2) generate a phenotyping feature neural network for multiple outcomes, and 3) represent patients as a phenotyping feature vector for each specific outcome.

Given multiple instances, a representative patient (e.g., center patient based on a mean average) can be identified so that in one group, if there are one hundred patients, the patient in the center (e.g., patient with minimal distance to other patients as defined by phenotype features) of the group can be selected as the representative patient. Representative patients can be determined via the following process: 1) form different groups according to outcome labels where patients in the same group have the same label; 2) for the groups of patients, cluster the patients into subgroups using outcome specific phenotyping features; and 3) for the subgroups, pick a center patient as the representative. Additionally, to filter patient data based on contextual data, the process can comprise: 1) selecting raw data events based on a condition associated with the outcomes for selected representatives; and 2) outputting the selected patients with the raw data events for the outcomes.

Given a pool of patients that are similar to each other, a subset of patients can be grouped together. The selection component 100 can then select from one or more patients to represent the group. Thus, the grouping component 102 can be configured to group one or more patients into a group based on outcome specific phenotyping features. For example, if susceptibility to a stroke (e.g., outcome) can be caused by high SBP or diabetes, then a first patient that has a high SBP can be clustered into the same group as a second patient that has diabetes. Then a representative patient comprising both phenotype features can be determined based on the similarity between high SBP and diabetes. Phenotyping features can be assigned a value associated with a likelihood to lead to a particular outcome. The value can be assigned from an external device or via a neural network as discussed later. The grouping component 102 can group patients based on the values associated with their respective phenotypes. If a patient's age is not a very high factor in determining the potential for a stroke, then the age data associated with the patient can be removed via the filtering component 104. For example, the patient's age data can be assigned a lower value than high SBP or diabetes as they relate to indicators for a stroke event. The filtering component can then filter out the age data based on a defined threshold value so that the age data is not taken into account for the grouping. Consequently, the selection component 100 can utilize the grouping data to determine phenotype feature value ranges associated with specific patients in relation to specific outcomes. The phenotype feature ranges can then be used to determine, which patient data is used to determine the representative patient.

Representative patients can be similar to their closest neighbors in a neighbor pool and dissimilar to other representatives with the same outcome. For example, in one pool, the representative patient can have a phenotype feature of high blood pressure that can lead to an outcome of a heart attack, and in another pool another representative patient can have a phenotype feature of high cholesterol, which can also lead to the same outcome of a heart attack. Furthermore, for the same patient pool, the patient representatives can be different according to a different outcome of interest.

For example, in a pool of ten patients where seven of the patients have phenotype features indicative of a heart attack, and three of the patients have phenotype features indicative of a stroke, the patient representatives will be different depending upon which outcome (e.g., heart attack or stroke) is being assessed. Even for the same outcome, context-relevant data can vary among different patients (e.g., age, weight). Given two different patients, the same types of phenotyping features can have different significance to the outcomes (e.g., age is more significant to heart attacks than it is for high blood pressure). Additionally, for the same patient, context-relevant events can vary among different outcomes (e.g., the patient's age is both an associated phenotype feature for a stroke and a myocardial infarction). Thus, given two different outcomes, different phenotyping features can be selected, based upon their assigned values, to return the outcomes for the same patient (e.g., age and SBP selected to return both stroke and heart attack outcomes for the same patient). Once the outcomes are Additionally, the selection component 100 can comprise a neural network component 110. The neural network component 110 can assist the selection component 100 in classifying phenotyping features and/or outcomes. Such classification can employ a probabilistic and/or statistical-based analysis to prognose or infer an action that can be performed. A support vector machine (SVM) is an example of a classifier that can be employed. The SVM can operate by finding a hypersurface in the space of possible inputs. Other directed and undirected classification approaches include, for example, naïve Bayes, Bayesian networks, decision trees, neural networks, fuzzy logic models, and probabilistic classification models providing different patterns of independence can be employed. Classification as used herein also may be inclusive of statistical regression that is utilized to develop models of priority. The disclosed aspects can employ classifiers that are explicitly trained (e.g., via a generic training data) as well as implicitly trained (e.g., via observing outcomes, receiving extrinsic information, and so on).

In various embodiments, the data associated phenotyping features, their similarities, and/or disparateness, can then be stored in a data store. The data can then be pulled from the data store to generate additional data as the selection component 100 data become more refined.

In one or more embodiments, identifying one or more patient representatives can comprise constructing and training probabilistic classifiers that learn to predict a probability distribution, meaning that the system can be trained to predict a probability distribution over one or more outcomes associated with various phenotyping features. In one embodiment, this can be performed using standard neural network training algorithms such as stochastic gradient descent with back propagation. For example, the selection component 100 can be trained, via the neural network component 110, to associate specific phenotypes (e.g., age, weight, SBP) of a patient with a probability that the patient belongs to a group of patients at risk for a heart attack. Consequently, the selection component 100 can predict that the patient has a defined percentage of likelihood of having a heart attack, and determine a representative patient from a patient pool of patients with phenotype features that correlate to having a heart attack.

As the neural network component 110 analyzes additional phenotypes and outcomes, the defined percentage of likelihood can be increased or decreased. For example, with regards to a heart attack outcome, on a value scale of one to ten, if both weight and SBP are given high values (e.g. seven and eight, respectively), and age is given a low value (e.g., three), then the neural network component can use this information to predict which phenotypes are relevant to specific outcomes for later iterations.

Additionally, if the selection component 100 determines that the phenotyping feature is actually not associated with a specific outcome or has a very low relevancy to a specific outcome, then the selection component 100 can decrease a weighted value (e.g., via a weighting component 204 discussed in FIG. 2) based on this determination. The decrease in weighted value can prompt the filtering component 104 to filter the phenotyping feature out based on a defined threshold value.

Figure 2:
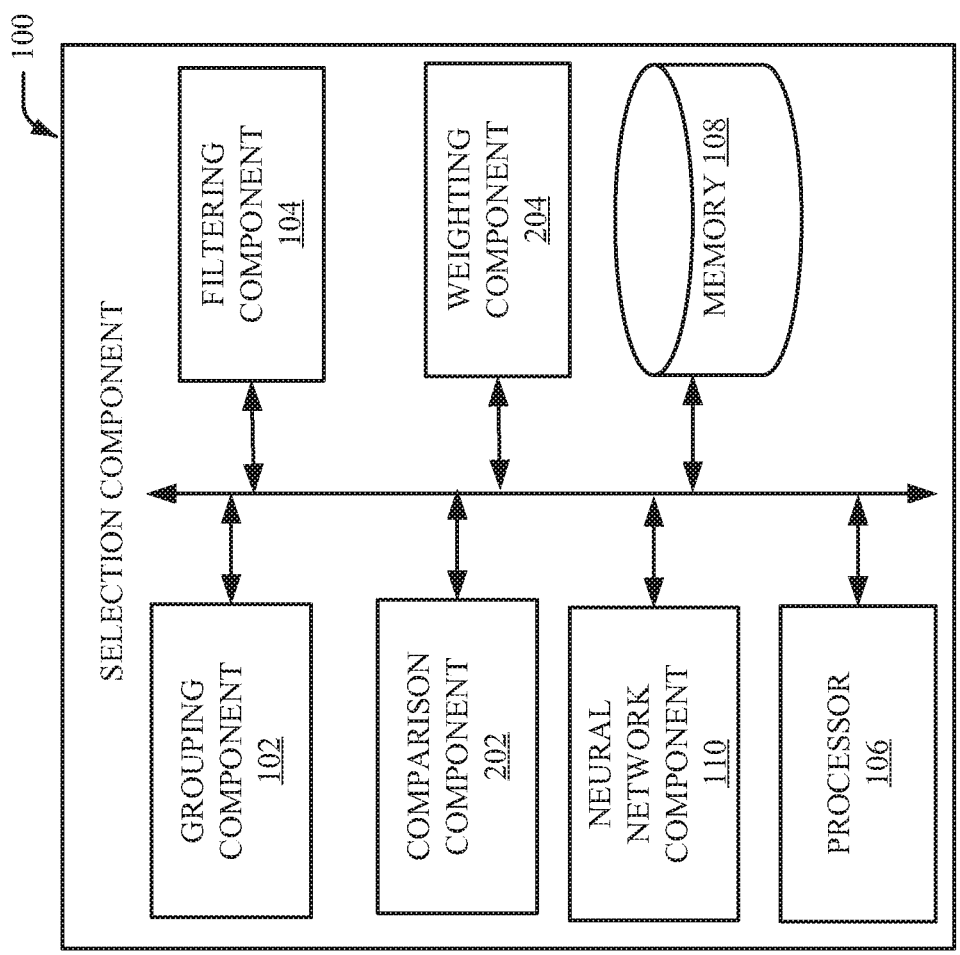
FIG. 2 illustrates a block diagram of an example, non-limiting system that facilitates neural network based selection of representative patients in accordance with one or more embodiments described herein.

FIG. 2 illustrates a block diagram of an example, non-limiting system that facilitates neural network based selection of representative patients in accordance with one or more embodiments described herein. Repetitive description of like elements employed in other embodiments described herein is omitted for sake of brevity.

In additional embodiments, the selection component can further comprise a comparison component 202 and a weighting component 204 which can be electrically and/or communicatively coupled to one another in various embodiments. The comparison component 202 can determine a similarity between a first phenotyping feature and a second phenotyping feature associated with one or more patients based on an outcome of interest. For example, a similarity between SBP and hypertension can be determined in relation to diabetes because an elevated SBP can be indicative of hypertension. Values associated with various phenotyping features in relation to predicted outcomes can be used determine the similarity between the phenotyping features. Accordingly, the phenotyping features can be assigned values in accordance with a particular outcome or the neural network component 110 can generate and assign the values based on previously analyzed data. Other phenotyping features can be taken into consideration also: time of elevated SBP, regularity of elevated SBP, duration of elevated SBP, etc. Consequently, these other phenotyping features can all have associated values that, in aggregate, determine the value for the elevated SBP.

The weighting component 204 can then represent the patients as a weighted vector of the phenotyping features via equation 1 below.

$$\sum_{i=1}^{T} a_i h_i$$ Equation (1)

Figure 6:
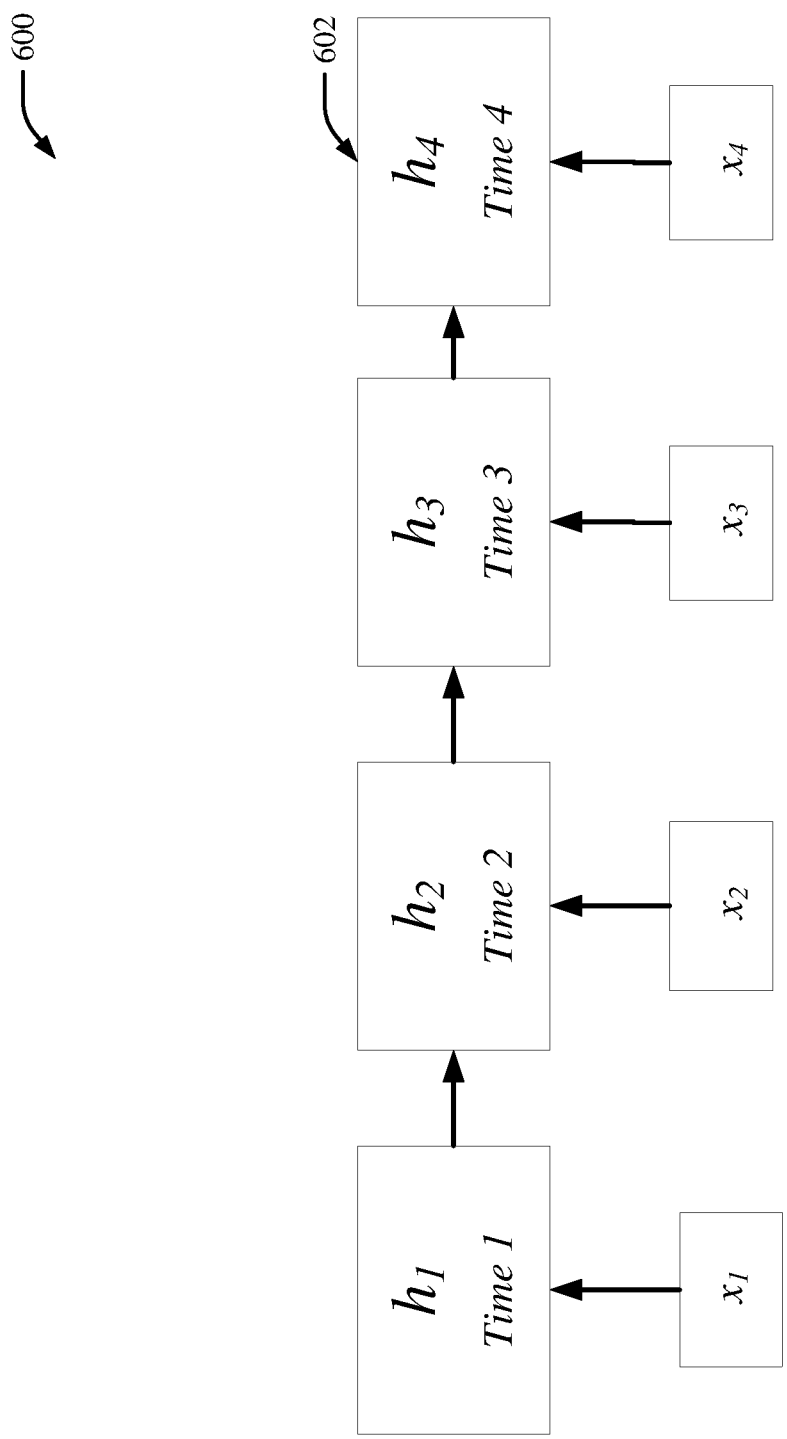
FIG. 6 illustrates an additional block diagram of example, non-limiting encoding process in accordance with one or more embodiments described herein.

Given a sequence of events $x_1, \ldots, x_T$ of a patient, as shown in FIG. 6, a sequence of hidden states $h_1, \ldots, h_T$ can be determined corresponding to the events by Equation (2) below. Additionally the attention weights of the hidden states compared to a specific outcome can be computed, and the weighted sum of the hidden states can be used as a representation of the patient. Thus, the weighted representation can be more accurate than $h_T$. Clustering (e.g., K-means) using the weighted vector can be used to select the patient representative with the minimum distance to other patients in the same group. It should be noted that any type of clustering model can be used, although K-means clustering can partition n observations patients) into k clusters (e.g., groups) in which the observations belong to the cluster with the nearest mean, serving as a representative of the group.

Because the weighting component 204 can weight phenotype features, a threshold can be selected to determine which phenotype features to keep to prevent the filtering component from filtering the phenotype features out. For example, if a threshold of zero is specified, then all phenotype features weighted above zero can be kept (or vice versa). However, if the phenotype feature is weighted below zero, the outcome can be filtered out via the filtering component 104 (or vice versa). Therefore, if the threshold is increased, then more or less phenotype features can be filtered out depending upon their weighted values. Additionally, if a patient has a sequence of phenotypes features, then the model can predict an outcome (e.g., via the neural network component 110) based on the sequence of phenotype features, in relation to their weighted values, as described later with reference to FIG. 6.

Figure 3:
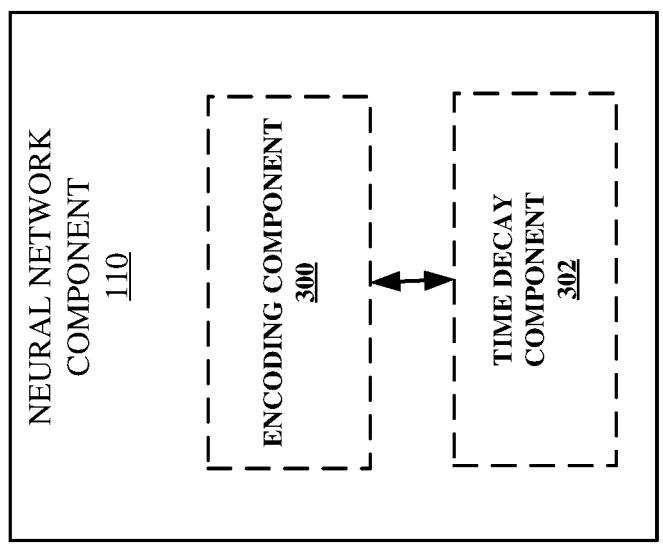
FIG. 3 illustrates a block diagram of an example, non-limiting system that facilitates neural network based selection of representative patients in accordance with one or more embodiments described herein.

FIG. 3 illustrates an additional block diagram of an example, non-limiting neural network component in accordance with one or more embodiments described herein. Repetitive description of like elements employed in other embodiments described herein is omitted for sake of brevity.

The neural network component 110 can comprise an encoding component 300 and a time decay component 302, which can be electrically and/or communicatively coupled to one another in various embodiments. It should be noted that in various embodiments, the neural network component 110 can comprise a recurrent neural network capable of encoding sequence data. For example, the neural network can encode phenotype feature sequence data into a vector and compute a representation of the phenotype feature sequence. Additionally, time stamps can be applied to the phenotype feature sequence data, wherein time stamps associated with the phenotype feature sequence data can be input into the recurrent neural network to generate the vector to represent the entire sequence. Therefore, the vector can represent the phenotyping features of a patient in relation to time. The neural network component 110 can also be configured to translate a phenotype feature sequence in one language to a phenotype feature sequence in another language by associating the weighted values of a phenotype feature in one language to weighted values of the same phenotyping features in another language.

The time decay component 302 can analyze a length of time associated with phenotyping features and/or their outcomes. Given a sequence of events to predict illness, the most recent events can be more relevant and important to the outcome. For example, if a patient currently has a phenotype feature (e.g., hypertension) that is indicative of a specific outcome (e.g. a stroke), then a weighted value associated with the phenotyping feature can be increased (via the weighting component 204) to a value higher than a weighted value for the same phenotyping feature associated with the patient three years ago. Consequently, the current phenotyping feature becomes more relevant in predicting a more current outcome than a phenotyping feature from three years ago. The weighted value can then be passed along to the filtering component 104 where the filtering component 104 can filter the three year-old phenotyping feature data out according to the defined threshold.

Figure 4:
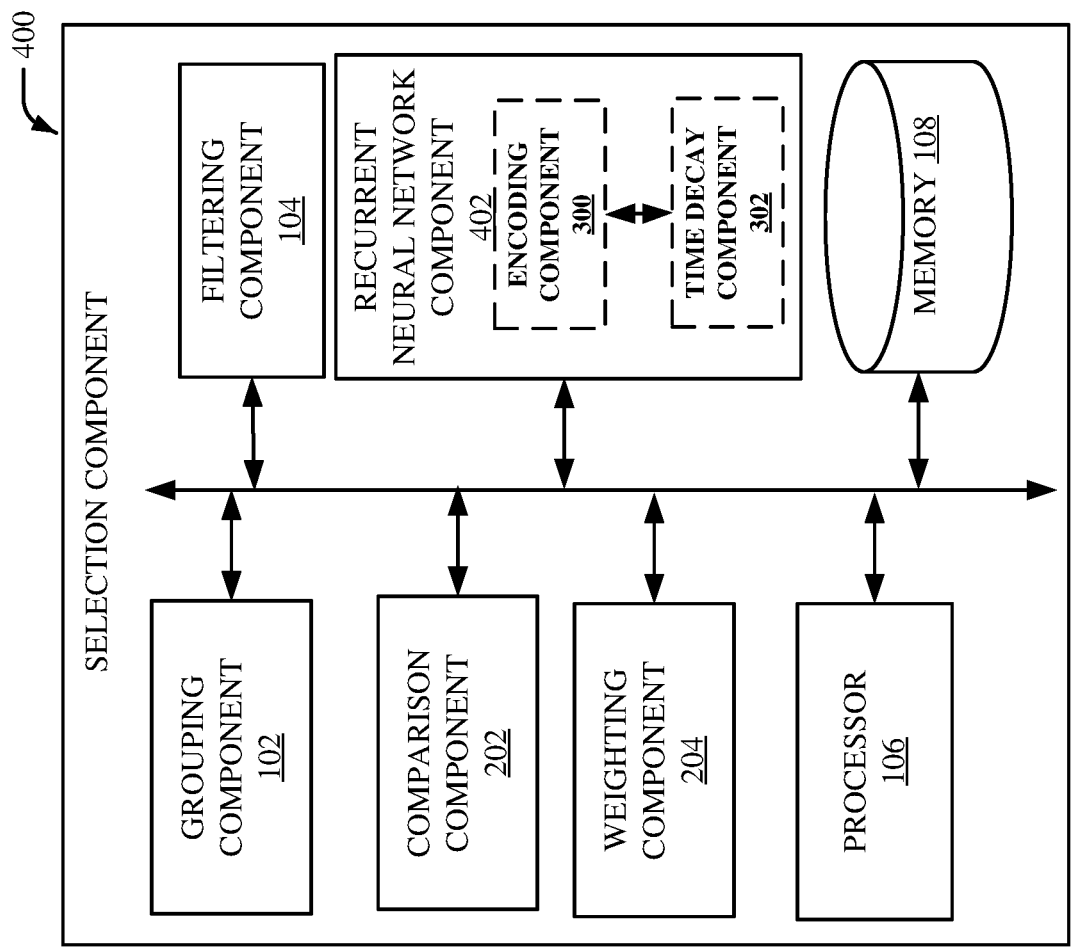
FIG. 4 illustrates an additional block diagram of an example, non-limiting neural network component in accordance with one or more embodiments described herein.

FIG. 4 illustrates a block diagram of an example, non-limiting system that facilitates neural network based selection of representative patients in accordance with one or more embodiments described herein. Repetitive description of like elements employed in other embodiments described herein is omitted for sake of brevity.

In another embodiment, the selection component 400 can comprise a recurrent neural network component 402. The recurrent neural network component 402 can be configured to propagate data forwards, but also backwards from later processing stages to earlier stages. Furthermore, the recurrent neural network component 402 can process arbitrary phenotype feature sequence data as noted in regards to FIG. 4. It should be noted that the recurrent neural network can vary (e.g., fully recurrent, recursive, Hopfield, etc.). For example, as the patient data pool becomes larger and the phenotype features associated with various outcomes become more precise, the weight value assigned to various phenotype features can be dynamically adjusted based on previous executions of the recurrent neural network. Consequently, more phenotype features will be filtered out via the filtering component 104 and the representative patients can be changed as the mean average is readjusted to reflect new phenotype feature data.

Figure 5:
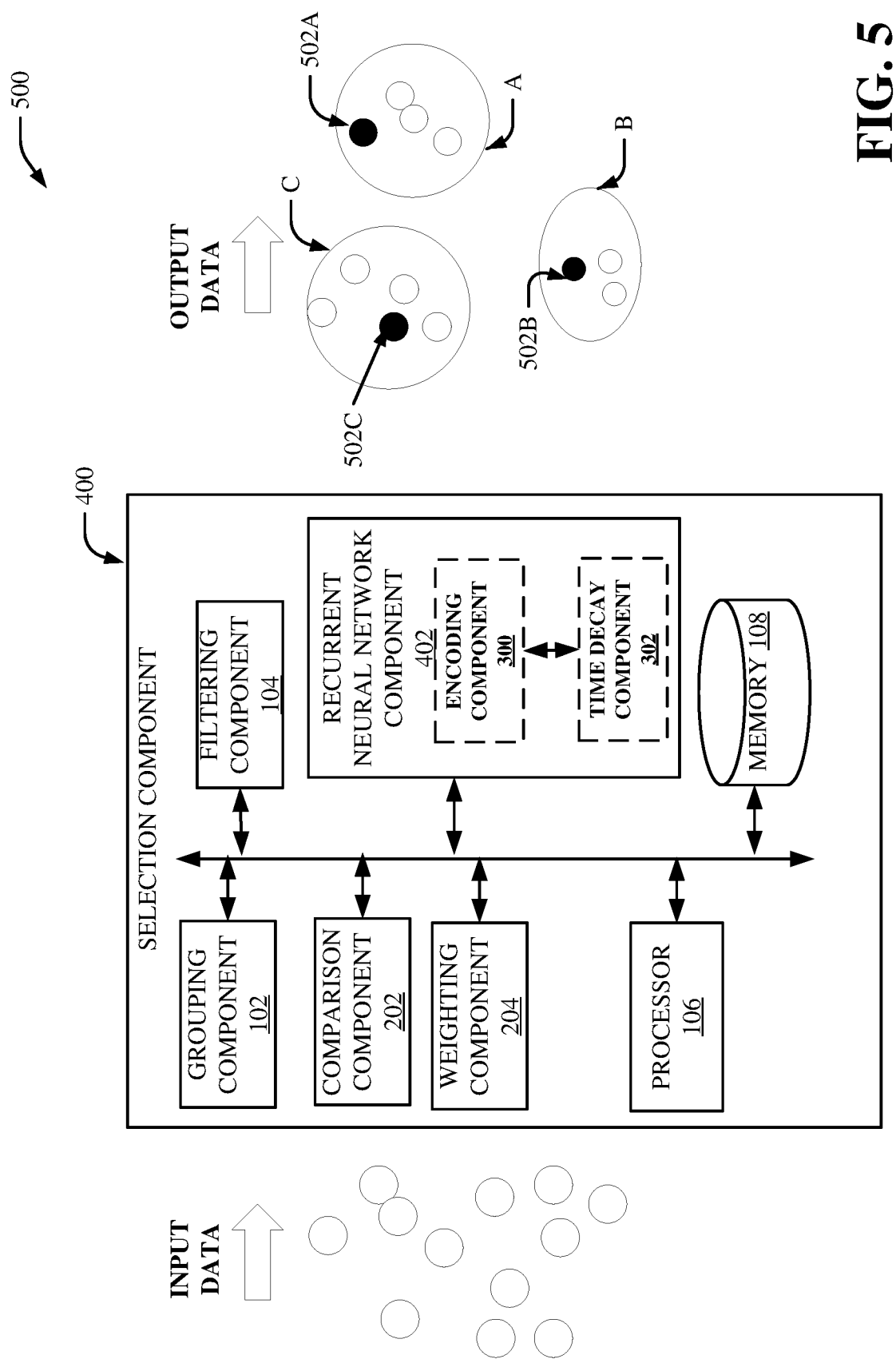
FIG. 5 illustrates an additional block diagram of an example, non-limiting system that facilitates neural network based selection of a representative patient in accordance with one or more embodiments described herein.

FIG. 5 illustrates an additional block diagram of an example, non-limiting system 500 that facilitates selection of a representative patient in accordance with one or more embodiments described herein. Repetitive description of like elements employed in other embodiments described herein is omitted for sake of brevity.

As depicted in FIG. 5, input data can be received by the selection component 400. The input data can comprise phenotypes and target outcomes associated with various patients. The comparison component 202 can determine a similarity between phenotyping features of patients based on values associated with the phenotyping features in relation to an outcome. Based on the determined similarity between phenotyping features, the grouping component 102 can group the patients into groups A, B, C. In the process of determining the representative patient, other phenotype data associated with susceptibility to strokes can be removed via the filtering component 104 to further refine the targeted outcome data. The filtering component 104 can then filter based on weighting data received from the weighting component 204. Additionally, as the recurrent neural network component 402 analyzes additional phenotype features and outcomes, the values associated with previous phenotyping features can be increased or decreased. K-means clustering can then be used to select the patient representative with the minimum distance to other patients in the same group. K-means clustering can partition the patients into groups based on the weighting data and identify representative patients 502A, 502B, 502C in relation to the targeted outcomes.

FIG. 6 illustrates an additional block diagram of example, non-limiting encoding process 600 in accordance with one or more embodiments described herein. Repetitive description of like elements employed in other embodiments described herein is omitted for sake of brevity.

It should be noted that in various embodiments, the recurrent neural network component 402 can comprise a recurrent neural network capable of encoding sequence data. For example, the neural network can encode a sequence of events into a vector. The last vector $h_4$ 602 can be used to represent or summarize the entire sequence and a weight for each state can be computed and summed for $h_{1-4}$ to provide a comprehensive representation of the sequence. The weight of hidden states can be computed against a specific outcome, such that for the same sequence, the weighted sum can be different for different outcomes.

Additionally, time stamps can be associated with the sequence data, wherein time stamps associated with the sequence data can be input into the recurrent neural network to generate the vector to represent the entire sequence. Therefore, the vector can represent the phenotyping features of a patient based on time.

For example, FIG. 6 depicts a sequence of events, which can be representative of data associated with a patient. To compute a weight, the events $x_{1-4}$ of the patient can be used to generate $h_{1-4}$, (e.g., phenotyping features) via Equation (2):

$$h_t = f(x_t, h_{t-1}), \text{ where } x_t \text{ is an event.} \qquad \text{Equation (2)}$$

Equation (2) can be utilized to encode a sequence of words into one or more vectors, wherein the last vector can summarize the entire sequence. Thus, $h_t$ can be used as an input to the selection component 400 to assist in outcome (e.g., $q_1$) prediction. Because the selection component 400 can utilize the recurrent neural network, weighting data can also be computed in accordance with the outcomes. Thus, the phenotype features, $h_1$ (e.g., phenotype feature), can be compared to the outcomes, $q_1$, via the comparison component 202, to determine to what extent $h_1$ correlates with $q_1$. If there is a high correlation, then the weight value associated with $h_1$ can be increased via the weighting component 204. Alternatively, if there is a low correlation, then the weight value associated with $h_1$ can be decreased via the weighting component 204.

Figure 7:
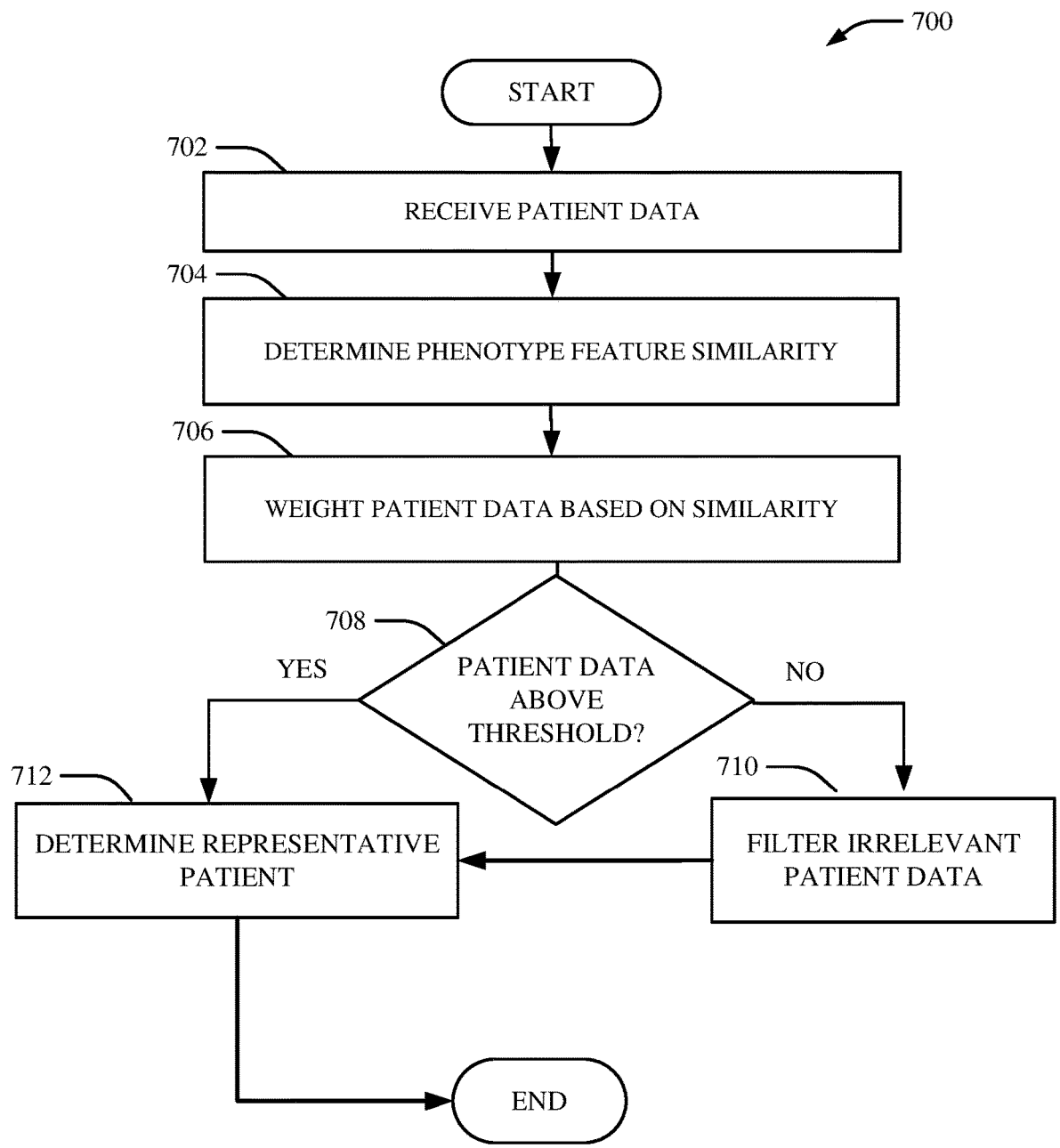
FIG. 7 illustrates a flow diagram of another example, non-limiting process that facilitates neural network based selection of representative patients in accordance with one or more embodiments described herein.

FIG. 7 illustrates a flow diagram of another example, non-limiting process 700 that facilitates neural network based selection of representative patients in accordance with one or more embodiments described herein. Repetitive description of like elements employed in other embodiments described herein is omitted for sake of brevity.

At block 702, the process can begin by receiving patient data associated with one or more patients into the selection component 100. The patient data can comprise various phenotyping features and/or a desired outcome associated with a patient. At element 704, a similarity between phenotypes of the patients can be determined (e.g., via the comparison component 202). For example, how close is the relation of weight to age when it comes to diagnosis of heart disease? Based on the relation (e.g., similarity) of weight to age, the phenotypes can be weighted (e.g., via the weighting component 204) accordingly, at element 706. Prior to the phenotyping features being weighted, a threshold value can be set (e.g., via the neural network component 110) to determine which phenotyping features should be filtered out during the process. Consequently, at element 708, the system can determine if the patient data weighted value is above the threshold value. If the patient data weighted value is below the threshold value, then the patient data can be filtered out (e.g., via the filtering component 104) at element 710. However, if the patient data weighted value is above the threshold value, then the patient data is included in determining a representative patient (e.g., via the grouping component 102) of the one or more patients at element 712.

Figure 8:
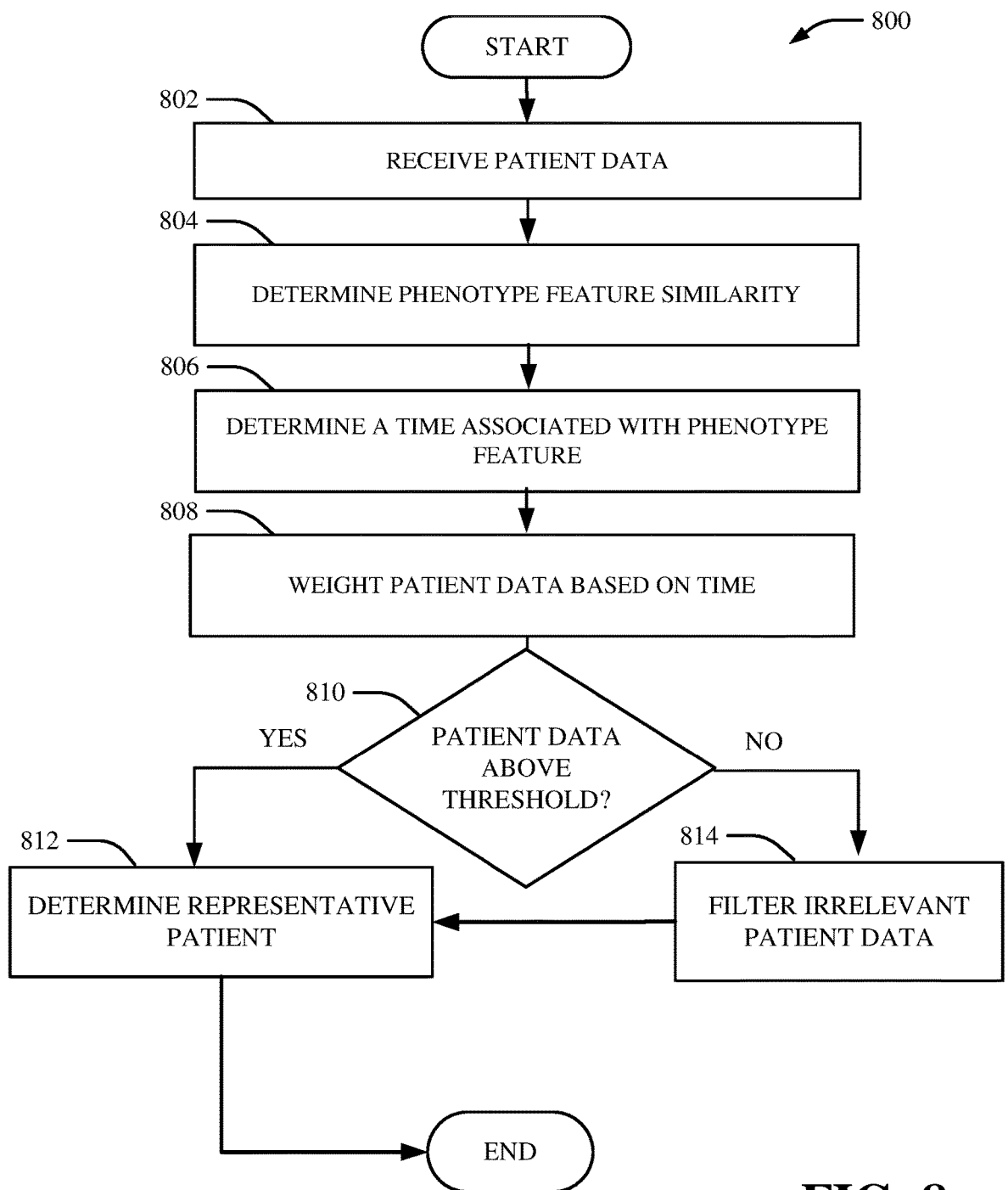
FIG. 8 illustrates a flow diagram of another example, non-limiting process that facilitates neural network based selection of representative patients in accordance with one or more embodiments described herein.

FIG. 8 illustrates a flow diagram of another example, non-limiting process 800 that facilitates neural network based selection of representative patients in accordance with one or more embodiments described herein. Repetitive description of like elements employed in other embodiments described herein is omitted for sake of brevity.

At block 802, the process can begin by receiving patient data associated with one or more patients into the selection component 100. The patient data can comprise various phenotyping features and/or a desired outcome associated with the patient. At element 804, a similarity between phenotyping features of the patients can be determined (e.g., via the comparison component 202). Additionally, at element 806 a time associated with the phenotype feature can be determined. For example, is the phenotyping feature a current indicator of the patient's health or is the phenotyping feature a past indication of the patient's health? Based on the time factor associated with the phenotyping feature, the phenotyping feature can be weighted (e.g., via the weighting component 204) accordingly, at element 808. Prior to the phenotyping feature being weighted, a threshold value can be set (e.g., via the neural network component 110) to determine which phenotypes should be filtered out during the process. For example, a weighted value given for a three-year old high blood pressure incident may be below the threshold value. Consequently, at element 810, the system can determine if the phenotyping feature weighted value is above the threshold value. If the phenotyping feature weighted value is below the threshold value, then the patient data can be filtered out (e.g., via the filtering component 104) at element 814 prior to a representative patient being determined at element 812. However, if the phenotyping feature weighted value is above the threshold value, then the patient data is included in determining the representative patient (e.g., via the grouping component 102) of the one or more patients at element 812.

Figure 9:
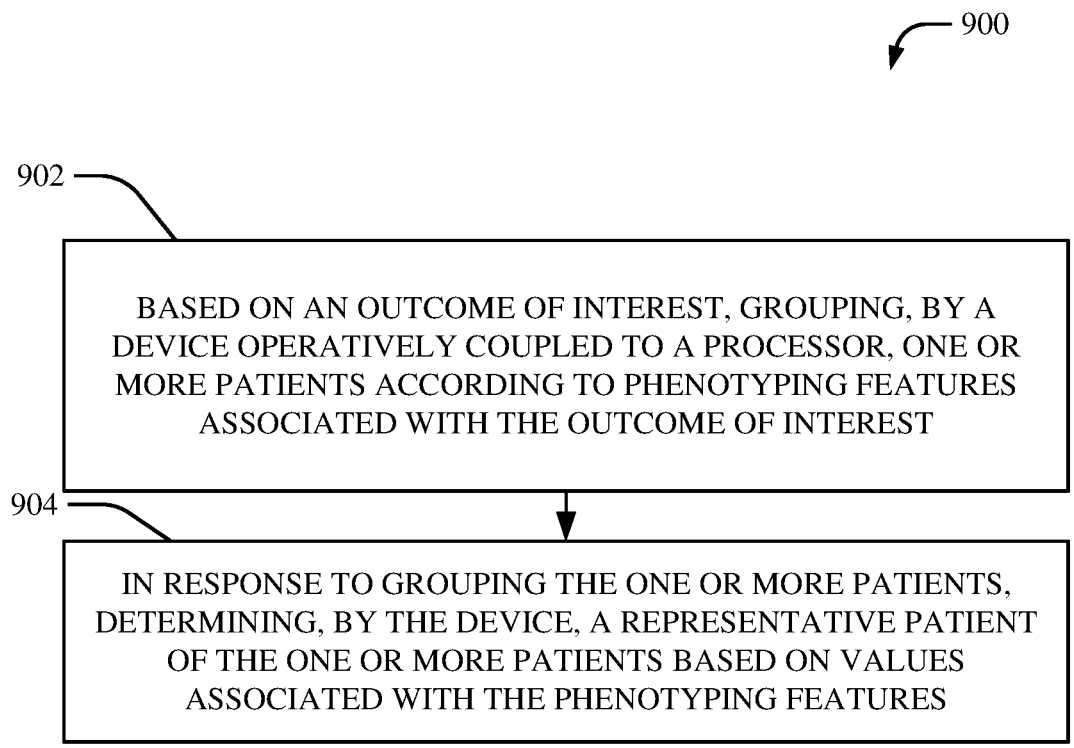
FIG. 9 illustrates a flow diagram of an example, non-limiting computer-implemented method that facilitates neural network based selection of representative patients in accordance with one or more embodiments described herein.

FIG. 9 illustrates a flow diagram of an example, non-limiting computer-implemented method 900 that facilitates representative patient in accordance with one or more embodiments described herein. Repetitive description of like elements employed in other embodiments described herein is omitted for sake of brevity.

Based on an outcome of interest, the method can comprise grouping (e.g., via the grouping component 102) one or more patients according to phenotyping features associated with the outcome of interest at element 902. The grouping component 102 can be configured to group one or more patients into a group based on outcome specific phenotyping features. For example, if susceptibility to a stroke (e.g., outcome) can be caused by high SBP or diabetes, then a first patient that has a high SBP can be clustered into the same group as a second patient that has diabetes. Phenotyping features can also be assigned a value associated with a likelihood to lead to a particular outcome. The value can be assigned from an external device or via a neural network. Therefore, the grouping component 102 can also group patients based on the values associated with their respective phenotypes.

In response to grouping the one or more patients, the method can also comprise determining (e.g., via the neural network component 110) a representative patient of the one or more patients based on values associated with the phenotyping features at element 904. The selection component 100 can be trained, via the neural network component 110, to associate specific phenotype features (e.g., age, weight, SBP) of a patient with a probability that the patient belongs to a group of patients at risk for a specific disease. Consequently, the selection component 100 can predict that the patient has a defined percentage of likelihood of having a heart attack, and determine a representative patient from a patient pool of patients with phenotype features that correlate to having a heart attack. It should be understood that as more patient data is received by the selection component 100, the selection component can refine data accordingly. For example, although weighted data can be filtered to determine a representative patient, the selection component 100 can also filter data (e.g., via the filtering component 104) based on the representative patient during an iterative execution of the process.

Figure 10:
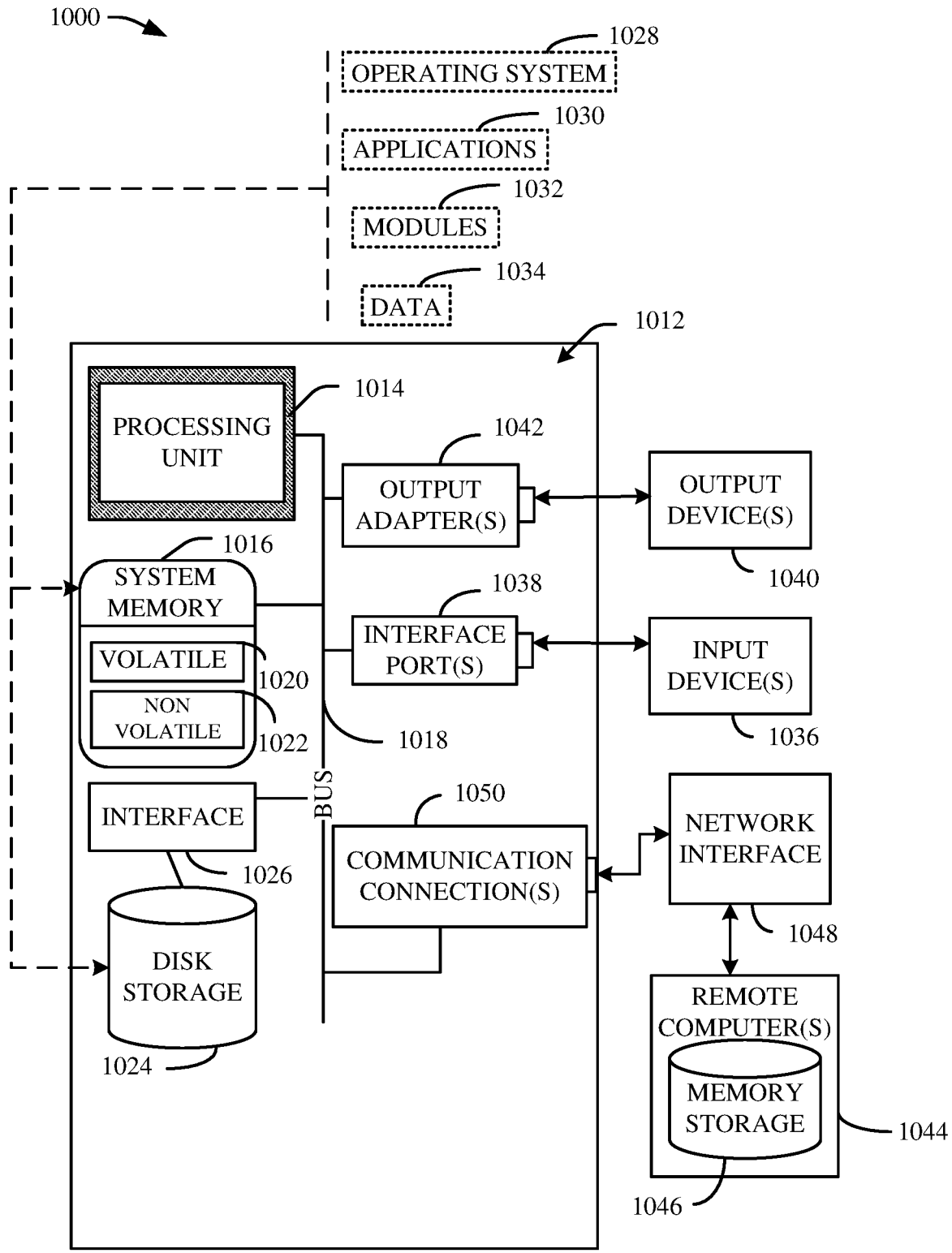
FIG. 10 illustrates a block diagram of an example, non-limiting operating environment in which one or more embodiments described herein can be facilitated.

In order to provide a context for the various aspects of the disclosed subject matter, FIG. 10 as well as the following discussion is intended to provide a general description of a suitable environment in which the various aspects of the disclosed subject matter can be implemented. FIG. 10 illustrates a block diagram of an example, non-limiting operating environment in which one or more embodiments described herein can be facilitated. With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012.

System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present disclosure may be a system, a method, an apparatus and/or a computer program product at any possible technical detail level of integration. The computer program product can include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
 a memory that stores computer executable components; and a processor that executes the computer executable components stored in the memory, wherein the computer executable components comprise:
  a neural network component that employs patient data to train a neural network comprising one or more probabilistic classifiers to predict a probability distribution over outcomes of interest associated with phenotyping features of patients in the patient data, wherein the neural network employs a stochastic gradient descent with back propagation algorithm to associate a phenotyping feature of the phenotyping features with an outcome of interest of the patients;
  a time decay component that generates, for each patient, using the neural network, a phenotype feature sequence vector comprising timestamped occurrences of phenotyping features and outcomes of interests in the patient;
  a weighting component that assigns, for each patient, using the neural network and the phenotype feature sequence vector, respective weights to pairs of the phenotyping features and the outcomes of interests based on respective amounts of time between first timestamps of occurrences of the phenotyping features in the patient and second timestamps of occurrences of the outcomes of interests in the patient;
  a grouping component that, based on an outcome of interest of the outcomes of interest:
    assigns, using the neural network, patients to groups according to phenotyping features associated with the outcome of interest, and filters out one or more of the patients, based on the respective weights of the phenotyping features for the patients for the outcome of interest and a threshold weight, from being utilized in determining a representative patient of the patients in a group for the outcome of interest;
  a comparison component that assigns, for each patient in the group, using the neural network, respective values to the phenotyping features of the patient; and
  a selection component that determines the representative patient of the patients in a group that has a minimal distance to other patients in the group based on the respective values associated with the phenotyping features of the patients in the group.

2. The system of claim 1, wherein the outcome of interest is associated with a target disease.

3. The system of claim 2, wherein the computer executable components further comprise:
  an encoding component that:
  encodes a sentence associated with the phenotyping features into a vector product to predict the target disease.

4. The system of claim 1, wherein the grouping component recursively assigns the patients to the groups according to a similarity between the phenotyping features and based on the outcome of interest.

5. The system of claim 1, wherein the respective values assigned to the phenotyping features are indicative of respective likelihoods of the phenotyping features leading to the outcome of interest.

6. The system of claim 1 wherein the grouping component employs K-means clustering.

7. The system of claim 1, wherein the comparison component that determines, based on the outcome of interest, a similarity between a first phenotyping feature and a second phenotyping feature of the phenotyping features associated with the patients.

8. A computer program product for employing neural networks to discover representative patients, the computer program product comprising a computer readable storage medium having program instructions embodied therewith, the program instructions executable to:
  train, using patient data, a neural network comprising one or more probabilistic classifiers to predict a probability distribution over outcomes of interest associated with phenotyping features of patients in the patient data, wherein the neural network employs a stochastic gradient descent with back propagation algorithm to associate a phenotyping feature of the phenotyping features with the an outcome of interest of the patients;
  generate, for each patient, using the neural network, a phenotype feature sequence vector comprising timestamped occurrences of phenotyping features and outcomes of interests in the patient;
  assign, for each patient, using the neural network and the phenotype feature sequence vector, respective weights to pairs of the phenotyping features and the outcomes of interests based on respective amounts of time between first timestamps of occurrences of the phenotyping features in the patient and second timestamps of occurrences of the outcomes of interests in the patient;
  assign, using the neural network, patients to groups according to phenotyping features associated with the outcome of interest;
  filter out one or more of the patients, based on the respective weights of the phenotyping features for the patients for the outcome of interest and a threshold weight, from being utilized in the determination of a representative patient of the patients in a group for the outcome of interest;
  assign, for each patient in the group, using the neural network, respective values to the phenotyping features of the patient; and
  determine the representative patient has a minimal distance to other patients in the group based on respective values associated with phenotyping features of the patients in the group.

9. The computer program product of claim 8, wherein the outcome of interest is associated with a target disease.

10. The computer program product of claim 9, wherein the program instructions are further executable to:
  encode a sentence associated with the phenotyping features into a vector product to predict the target disease.

11. The computer program product of claim 8, wherein the assignment occurs recursively according to a similarity between the phenotyping features and based on the outcome of interest.

12. The computer program product of claim 8, wherein the respective values assigned to the phenotyping features are indicative of respective likelihoods of the phenotyping features leading to the outcome of interest.

13. The computer program product of claim 8, wherein the grouping employs K-means clustering.

14. The computer program product of claim 8, wherein the program instructions are further executable to:
  based on the outcome of interest, determine a similarity between a first phenotyping feature and a second phenotyping feature of the phenotyping features associated with the patients.

15. A computer-implemented method, comprising:
  training, by a device operatively coupled to a processor, using patient data, a neural network comprising one or more probabilistic classifiers to predict a probability distribution over outcomes of interest associated with phenotyping features of patients in the patient data, wherein the neural network employs a stochastic gradient descent with back propagation algorithm to associate a phenotyping feature of the one or more phenotyping features with the an outcome of interest of the patients;

generating, by the device, for each patient, using the neural network, a phenotype feature sequence vector comprising timestamped occurrences of phenotyping features and outcomes of interests in the patient;

assigning, by the device, for each patient, using the neural network and the phenotype feature sequence vector, respective weights to pairs of the phenotyping features and the outcomes of interests based on respective amounts of time between first timestamps of occurrences of the phenotyping features in the patient and second timestamps of occurrences of the outcomes of interests in the patient;

assigning, by the device using the neural network, patients to groups according to phenotyping features associated with the outcome of interest;

filtering out, by the device, one or more of the patients, based on the respective weights of the phenotyping features for the patients for the outcome of interest and a threshold weight, from being utilized in the determination of a representative patient of the patients in a group for the outcome of interest;

assigning, by the device, for each patient in the group, using the neural network, respective values to the phenotyping features of the patient; and determining, by the device, the representative patient has a minimal distance to other patients in the group based on respective values associated with phenotyping features of the patients in the group.

16. The computer-implemented method of claim 15, wherein the outcome of interest is associated with a target disease.

17. The computer-implemented method of claim 16, further comprising:

encoding, by the device, a sentence associated with the phenotyping features into a vector product to predict the target disease.

18. The computer-implemented method of claim 15, wherein the respective values assigned to the phenotyping features are indicative of respective likelihoods of the phenotyping features leading to the outcome of interest.

* * * * *